United States Patent [19]

Sealfon

[11] Patent Number: 5,336,189
[45] Date of Patent: Aug. 9, 1994

[54] COMBINATION IV PUMP AND DISPOSABLE SYRINGE

[76] Inventor: Andrew I. Sealfon, 17 Industrial Pl., Middletown, N.Y. 10940

[21] Appl. No.: 110,699

[22] Filed: Aug. 23, 1993

[51] Int. Cl.$^5$ .................................. A61M 37/00
[52] U.S. Cl. .................... 604/135; 604/246; 128/DIG. 12
[58] Field of Search ........... 604/154, 155, 187, 197, 604/218, 228, 232, 222, 151, 152, 153, 131, 135, 51; 128/DIG. 1

[56] References Cited

U.S. PATENT DOCUMENTS

| | | | |
|---|---|---|---|
| 4,298,000 | 11/1981 | Thill et al. | 604/135 |
| 4,300,554 | 11/1981 | Hessberg et al. | 604/135 |
| 4,313,439 | 2/1982 | Babb et al. | 604/135 |
| 4,677,980 | 7/1987 | Reilly et al. | |
| 4,701,165 | 10/1987 | DeHaitre | |
| 4,755,172 | 7/1988 | Baldwin | 604/131 |
| 4,997,420 | 3/1991 | LeFevre | 604/131 |
| 5,261,882 | 11/1993 | Sealfon | 604/246 |

*Primary Examiner*—C. Fred Rosenbaum
*Assistant Examiner*—N. Kent Gring

[57] ABSTRACT

A facilitated procedure for attaching single-use syringes, one at a time, to an intravenous (IV) pump in which each syringe is mounted in the path of the IV pump plunger by clips and within a clear plastic syringe-holding sleeve that overlies the volumetric graduations of the syringe to permit visual monitoring of the exiting flow, and permits an operating mode using plural pre-filled syringes for IV therapy using the same IV pump.

4 Claims, 2 Drawing Sheets

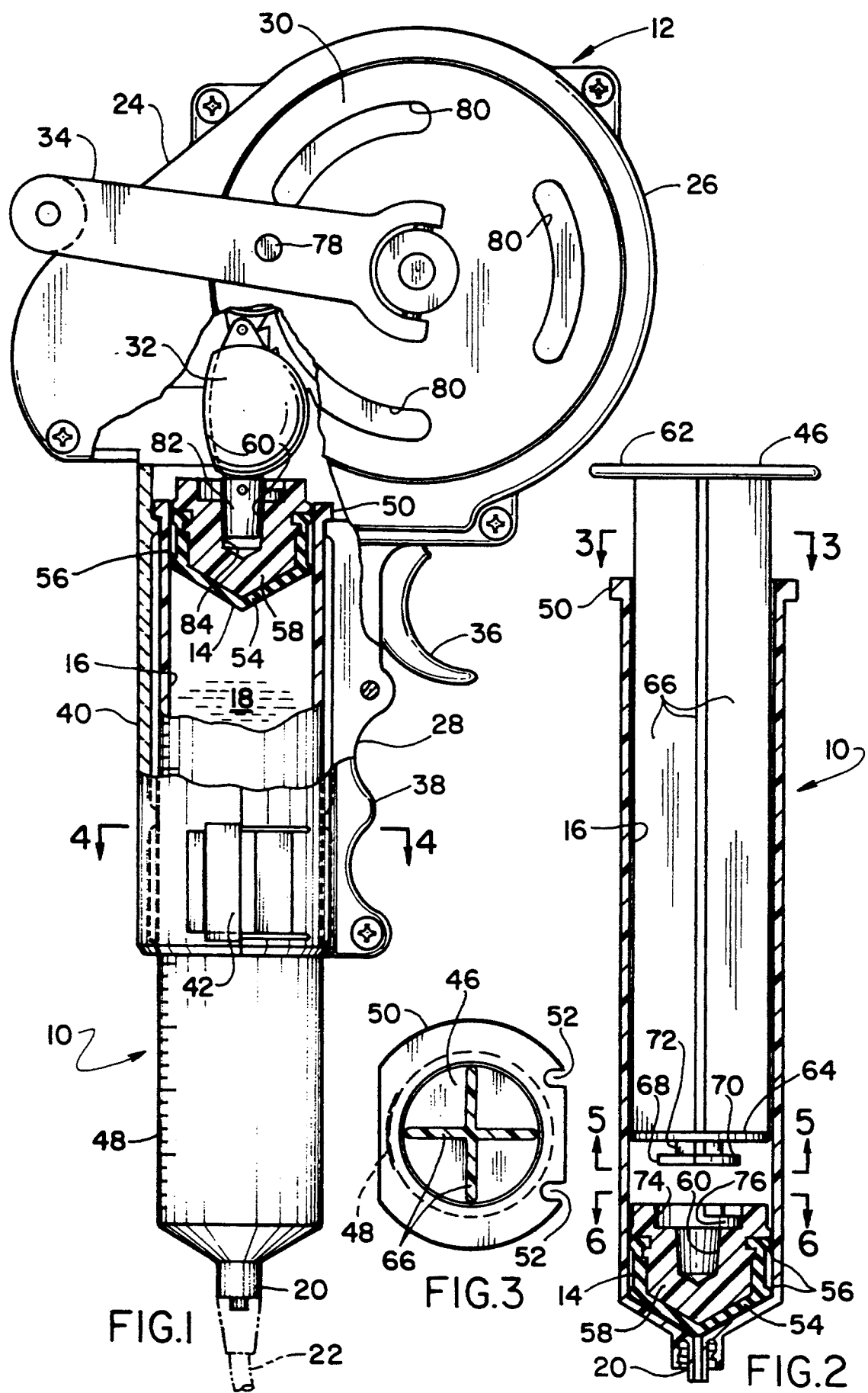

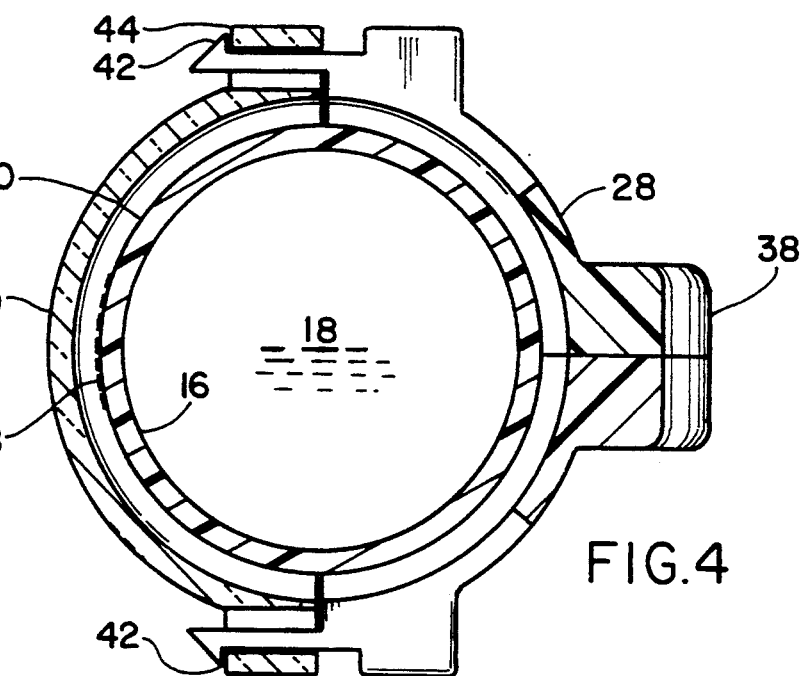
FIG.4
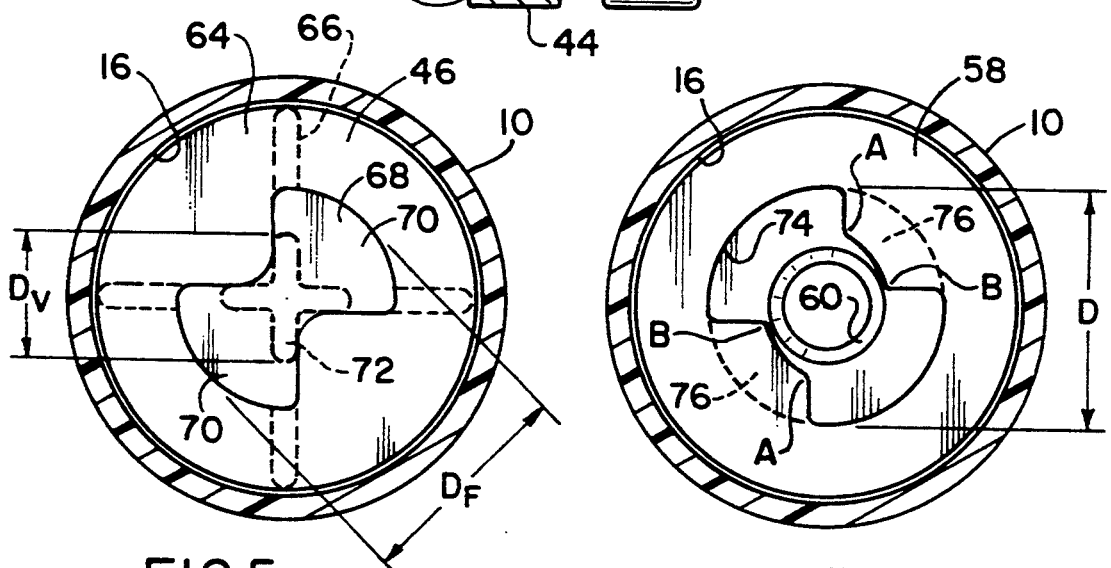
FIG.5
FIG.6
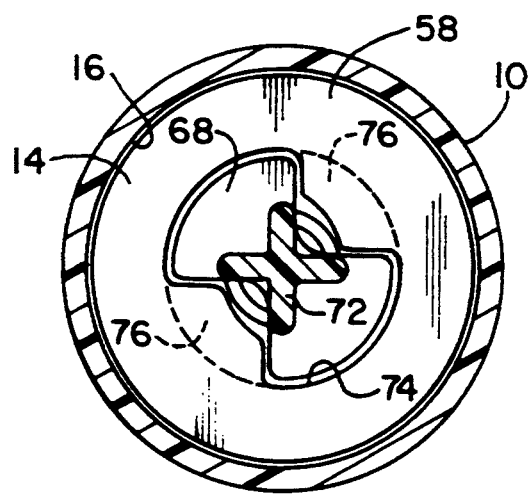
FIG.7
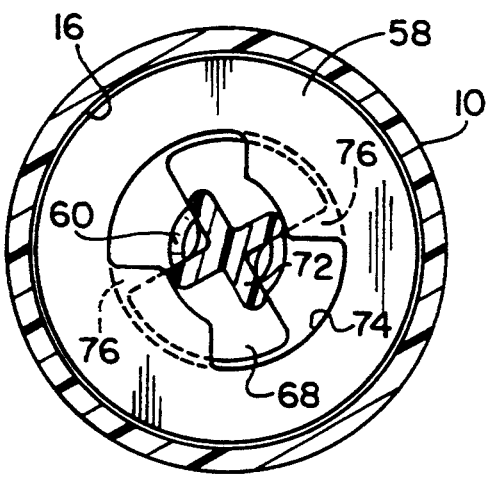
FIG.8

COMBINATION IV PUMP AND DISPOSABLE SYRINGE

The present application is related to application Ser. No. 053,873 filed Apr. 26, 1993 now U.S. Pat. No. 5,261,882, incorporated herein by reference.

The present invention relates generally to improvements for intravenous (IV) therapy, the improvements more particularly contributing to an advantageous and facilitated procedure for filling or loading disposable syringes for storage under sterile conditions and use, one at a time, with an IV pump, preferably of compact size.

The referenced compact-sized IV pump is ideally a portable non-electric intravenous (IV) pump specifically intended for portable ambulatory therapy at an optimum low cost, and, more particularly, to an improved IV pump which, in practice, contributes to providing intravenous therapy without a patient being "lassoed" to a hospital bed, or having to wheel an IV pole, in a hospital or at home. The IV pump thus allows a patient, who is otherwise able to walk, to receive therapy outside of the hospital with an effective, low cost IV system. An acceptable tradeoff, however, is that the plunger is not of a nature that can fill the syringe acted upon by the pump and, thus, the syringe-filling operation is done prior to the interconnection of a filled syringe to the IV pump, during which it is necessary to use a straight, aptly referred to "bayonet" type plunger, adapted to engage a syringe piston and withdraw the piston axially of the syringe barrel incident to filling the syringe with IV medicant.

Examples of the Prior Art

There is already disclosed in the prior art syringes for operative connection to an IV pump of choice, for use, one at a time, in providing IV therapy. The plunger-to-piston engagement, filling of the syringe, and disengagement of the syringe-filling plunger in favor of the IV pump plunger of this prior art, unfortunately, is not entirely satisfactory. Exemplary of this prior art is U.S. Pat. No. 4,677,980 issued Jul. 7, 1987 to D. M. Reilly, et al. which uses hooks 184 cammed through closing movement upon a syringe piston and under spring urgency 186 released therefrom, which operating mode is relatively complex.

Likewise, in U.S. Pat. No. 4,701,165 issued Oct. 20, 1987 to Lon DeHaitre, although the threadable engagement established between the syringe-filling plunger and piston is relatively simple, the disengagement by unthreading provides a threaded bore for subsequent engagement to the IV pump plunger, which is not advantageous for use under the circumstances since neither the end of the IV pump plunger nor the piston of the syringe to be attached thereto has a rotative degree of movement.

Broadly, it is an object of the present invention to provide a combination IV pump of choice and a single-use, disposable syringe, overcoming the foregoing and other shortcomings of the prior art. More particularly, it is an object to achieve facilitated interengagement of the IV pump plunger and a strategically located syringe piston using to advantage initial urgency in the power stroke of the IV pump, all as will be explained in detail subsequently.

The description of the invention which follows, together with the accompanying drawings, should not be construed as limiting the invention to the example shown and described, because those skilled in the art to which this invention appertains will be able to devise other forms thereof within the ambit of the appended claims.

FIG. 1 is a front elevation, partly in section, of an IV pump of choice and, in interconnected relation therewith, a filled disposable-type syringe preparatory to use;

FIG. 2 is an isolated vertical section of the syringe of FIG. 1 illustrating how the syringe is filled using a special syringe-filling plunger for this purpose incident to the connection of the syringe to the IV pump of FIG. 1;

FIG. 3 is a cross-sectional view as taken along line 3—3 of FIG. 2;

FIG. 4 is a cross-sectional view as taken along line 4—4 of FIG. 1;

The remaining figures illustrate, in sequence, the manner in which the referred-to special syringe-filling plunger is attached to a piston of the syringe. More particularly, FIG. 5 is a cross-sectional view as taken along line 5—5 of FIG. 2 illustrating details of the connecting structure of the plunger;

FIG. 6 is also a cross-sectional view, but taken along line 6—6 of FIG. 2, and best illustrates the cooperating connecting structure of the syringe piston;

FIG. 7 is a cross-sectional view similar to FIG. 6, but illustrating the positioning of the plunger preparatory to engagement to the piston; and FIG. 8 is another view similar to FIG. 7 and illustrating the plunger in its engaged relation to the piston.

As explained in my presently pending U.S. patent application filed Apr. 26, 1993 for "A Negator Spring-Powered Syringe" and assigned Ser. No. 053,873, now U.S. Pat. No. 5,261,882 in connection with which any patent granted thereon by this reference is to be understood to be incorporated in its entirety herein, it is highly desirable to have an IV pump adapted to be worn or supported on a patient's belt during ambulatory use, of which the IV pump generally designated 12 in FIG. 1 is to be understood to be an example. This category of IV pump should be compact in size. To achieve this compactness, the plunger of the IV pump of the pending application is formed by interconnected spheres 32, and its power stroke travel is along a circular rather than straight line path, wherein the size difference between the pump housing for the former (circular) and what would be required for the latter (straight) being significantly less and consequently correspondingly contributing to the compactness in size of the IV pump 12. An acceptable trade-off, however, is that the circular plunger of interconnected spheres 32 can only effectively expel IV fluid, but cannot fill the syringe 10 acted upon by the pump, and, thus, the syringe-filling operation is done prior to the interconnection of a filled syringe 10 to the IV pump 12.

Moreover, since there is no size restriction that has to be considered in the syringe-filling operation, a straight plunger 46 of conventional and of well known design in many respects is used for this purpose. It will be explained in detail subsequently, however, what structural features and operating mode are provided to the plunger to enable it to be readily initially attached, used to fill, and then subsequently detached from the syringe 10, which syringe then in turn is readily attached to the IV pump 12 and, thus, is in condition for IV-delivering service to a patient. More particularly, the just-noted syringe-filling and facilitated operative association thereof to an IV pump, such as pump 12, is the crux of the within invention.

As background to understanding the syringe-filling and use requirements, structural details and operating parameters of the IV pump 12 are helpful to be first provided in connection with FIG. 1, to which figure reference should now be made. In FIG. 1 is shown a previously filled or loaded syringe 10 attached to, and thus ready for use in response to the power stroke of the IV pump 12, preferably of my referenced pending application. Pump 12 uses a negator spring to urge a piston 14 located as shown in the upper opening of barrel 16 of a syringe 10 along the length of barrel 16 and during this path of movement expels fluid medicant 18 through a luer-lock outlet 20 and through a catheter 22, which will be understood to be attached thereto. Catheter 22 as understood is fitted with an IV needle (not shown) for intravenous delivery of the medicant 18 to a patient.

For the purposes noted, pump 12 has a housing 24 of a generally oblong-circular shape denoted by the reference numeral 26, and completed with a lower depending generally cylindrically shaped handle section denoted by the reference numeral 28. The oblong-circular shaped section 26 functions as a housing for a negator spring-powered drive train 30 which consists of the inter-connected spheres 32 arranged in a generally circular, or non-linear orientation, so as to occupy a nominal amount of space. A foldable crank 34 is used to load the negator driving spring which, following the loading thereof, is then released to supply the powering force for the power stroke, using a trigger release 36 in an appropriate manner, an explanation of which is not necessary for an understanding of the present invention.

Pertinent to the within invention in permitting the facilitated attachment of a filled or loaded syringe 10 to the pump 12 are the components of FIG. 1 which will now be referred to. Among other components provided to this useful purpose and end is the formation in the lower cylindrical handle section of a shaped pistol-grip 38 constructed to have a removable, transparent left side, as viewed in FIGS. 1 and 4, denoted by the reference numeral 40. Using the transparency of the plastic construction material of the handle section 40, a user can visually see the graduations 48 (FIG. 3) of the attached syringe barrel 16 and, thus, monitor the amount of the medicant 18 being delivered from the syringe 10. As best shown in FIG. 4, the other half of the handle section 28 has attached to it the just-referred-to transparent half 40 such that the two halves, 28 and 40, are in encircling relation about the syringe barrel 16. This is achieved using a pair of spring clips 42 integral with the handle section 28 wherein the distal ends of the clips 42 are appropriately disposed through, and held in place, by latch means 44. To disconnect or unlatch the springs 42, the ends thereof are closed towards each other in the clearances provided and then eased in a direction to the right as viewed in FIG. 4, from the latch means 44.

In the contemplated use with the IV pump 12, a syringe 10 is first supplied to a pharmacist for filling under sterile conditions wherein a syringe piston 14 will be inserted to the distal end of the barrel 16, as shown in FIG. 2. Next, a plunger 46 will be inserted in the barrel 16 to a position adjacent the piston 14, again as is best shown in FIG. 2. At this point it is significant to note two orientations or relative positions of the components. First, in the subsequent attachment of the filled syringe 10 to the IV pump 12, it is desirable that the volume indicia 48 be presented beneath the previously-noted transparent section 40 of the handle grip 28 so as to be readily readable to the user. To this end, the upper end of the barrel 16 is provided with a flange 50 which, as best shown in FIG. 3, has holes or slots 52 which it will be understood are used to register with appropriate male members in housing 24 (not shown) to thereby assure the positioning of the barrel volume indicia 48 directly behind the transparent portion 40 of the hand grip 28.

The other orientation requirement involves the interconnecting of the lower end of the plunger 46 with the upper end of the piston 14, a procedure which is illustrated in sequence in FIGS. 5-8 inclusive. Underlying one of the significant aspects of the present invention is the recognition that the positioning of the lower end of the plunger 46 in relation to the upper end of the piston 14 is facilitated by the fact that the plunger 46 has a rotative degree of movement within the barrel 16 and thus using this degree of movement to achieve the initial connection of the plunger 46 to the piston 14, and then subsequently readily disconnecting these components again using a rotational traverse, i.e. first in a clockwise direction (attaching) and then in a counter-clockwise direction (unattaching). First, however, it is to be noted that piston 14 has an outer member 54 of elastomeric construction material and is contoured to have annular seals 56 to obviate leakage past the piston. A rigid core-like member 58 is disposed within a compartment formed within outer member 54 to insure piston stability and mainly to provide a coupling socket 60. Plunger 46, preferably of rigid plastic construction material, has at its opposite ends an upper gripping flange 62 and a lower smaller-size flange 64. Connected in spanning relation between the flanges 62 and 64 is the body of the plunger 46 formed as a criss-crossing vertical vane 66. Vane 66 and flange 64 are sized to provide clearance for axial movement of the plunger 46 within the syringe barrel 16. Provided on the lower face of flange 64 is a depending key member 68 having, as best understood from FIGS. 5-8, two oppositely laterally extending segments 70 to achieve engagement to cooperating structure in the piston socket 60. More particularly, starting first with FIG. 5, it will be noted that the key segment 68 is attached to the lower face of flange 64 by an interposed short length of four equally spaced apart arrangements of a vertical and radial extending vane 72, thus providing a clearance which is the height of the vane 72. Segment 68 is appropriately shaped to fit within a similarly shaped opening 74 in the upper surface of the piston core member 58. When piston 14 is to be engaged by plunger 46 the user lowers plunger 46 into barrel 16 and, by feel, permits flange 68 to drop through opening 74, whereupon clockwise movement of plunger 46 will lock the segment 68 to piston 14. In FIGS. 5-8 it will thus be noted that opening 74 has an outside diameter D (FIG. 6), a diameter DA between opposed corners A (again FIG. 6), and another smaller diameter DB (FIG. 6) between opposed corners B. As a consequence, opposed length portions A-B overhang an undercut 76 in core member 58. Key 68 has an outside diameter DF (FIG. 5) and short vane 72 has a diameter DV (again FIG. 5).

When segment 68 is inserted within opening 74 and into cavity 76, it has a degree of rotative movement in a clockwise direction, as viewed in FIG. 7, and this is imparted until vane 72 engages the converging edges of curves A-B. Thus, it should be readily understood, will occur because dimension D is slightly greater than dimension DF; the dimension DA is slightly greater than the dimension DV; and the dimension DV is slightly greater than the dimension DB. Stated otherwise, vane 72 will jam on the gradually decreasing inside diameter of opening 74 bounded by the length portions A–B, thereby resulting in an interference or friction fit which provides the requisite locking or holding force between the piston 14 and plunger 46. As may best be understood by comparing FIGS. 7 and 8, it will be noted that the component parts are dimensioned to permit approximately a 60 degree rotational traverse in a clockwise rotation of plunger 46 relative to piston 14 before the locking referred to is established or occurs. When plunger 46 is secured to piston 14, the user then connects outlet 20 to an appropriate source of fluid medication 18. The user then proceeds to retract piston 14 to the desired level in syringe 10. Before plunger 46 is removed, it is recommended that the user place the syringe with the outlet up and expel any air that inadvertently might have entered into the barrel 16, following which the syringe 10 is capped at the outlet 20. Syringe 10 is now in condition for storage and eventual IV service to the patient by being attached to the IV pump 12, a procedure which will now be described.

Preparatory to use of the IV pump 12 in conjunction with the filled or loaded syringe 10, the user will first unfold crank 34 and orient a pin extension 78 on crank 34 to fit one of three arcuate sockets 80 on the drive train 30. Drive train 30 is then moved into position in which, as illustrated in FIG. 1, the leading sphere 32 is adjacent the exit opening of the housing for the pump 12, at which exit opening the filled or loaded syringe 10 is, of course, to be attached to the pump 12. In practice, a crank traverse of approximately 210 degrees clockwise will achieve the positioning of the lead sphere 32 mentioned, it being assumed that the interconnected spheres 32 have just been urged through a power stroke resulting in these spheres being projected through the housing opening and thus the 210 degree crank traverse will effectively retract the non-linear linkage 32 within the housing 26 and provide the lead sphere 32 with the position illustrated in FIG. 1. Handle section 40 is then removed after unlatching the two clips 42 from each latch 44. Any empty syringe 10 which may be present is disposed of. A full or loaded syringe is then readied for attachment to the pump 12, care being taken at this time to align the slots 52 previously mentioned. The actual attachment of the lead sphere 32 is achieved using a stud fitting 82 extending from the sphere which is projected into a tapered seat 84 of coupling socket 60, relying on the friction or inter-fit that is established, and then optionally supplementing the engaged relation with a pin or the like. Naturally, since the power stroke is in the direction of the taper of the stud fitting 82 in relation to the cooperating taper of the coupling socket 60, the inadvertent disengagement of the stud fitting 82 from the tapered seat 84 is, of course, not likely.

After alignment of the slots 52 provided on the finger grip flange 50, the transparent half or component 40 is replaced in encircling relation about the filled syringe 10 and secured in place using the spring clips 42. The closure or cap previously placed over the outlet 20 to preserve sterile conditions, is then removed and a catheter 22 connected to the outlet 20. Trigger 36 is then actuated to actually achieve the interconnection of the stud fitting 82 within the coupling socket 60 previously mentioned, wherein the spring urgency of the negator spring which powers the drive train 30 to advance the lead sphere 32 and thus the stud fitting 82 projecting therefrom into the correspondingly tapered seat 84.

Upon engagement of the stud fitting 82 in its seat 84, piston 14 starts to move through a power stroke, in a well understood manner in connection with spring-powered IV pumps, to thereby force or expel the fluid medication 18 from the syringe housing 16 through the outlet 20 and into the catheter, it being understood that the needle end of the catheter 22 (not shown) is appropriately attached for intravenous delivery of the medicant 18 to a patient.

It should be readily understood from the preceding description that there has been described an advantageous and facilitated procedure for filling or loading disposable syringes for storage under sterile conditions and use, one at a time, with an IV pump, preferably of compact size, in which the plunger thereof is circular to promote compactness in size and, thus, not particularly suitable for filling the syringe, but very effective for expelling or delivering the IV fluid to a patient.

While the apparatus herein shown and disclosed in detail is fully capable of attaining the objects and providing the advantages hereinbefore stated, it is to be understood that it is merely illustrative of the presently preferred embodiment of the invention, and that no limitations are intended to the detail of construction or design herein shown other than as defined in the appended claims.

What is claimed is:

1. An IV pump of a type having a housing with an exit opening and a plunger operatively arranged within said housing to partake of a power stroke along a path of movement through said exit opening and for a selected distance lengthwise thereof, a semi-circular sleeve mounted in depending relation from said housing having an upper end portion in alignment with said exit opening and having an orientation along said path of movement of said IV pump plunger, a cooperating pair of clip means adjacent said upper end of said sleeve, a disposable cylindrically-shaped syringe filled with fluid sized to fit in said sleeve operatively disposed to be engaged by said clip means so that said IV pump plunger power stroke is directed into said syringe, and a slidably disposed piston in an interposed position between said IV pump plunger and said fluid contents of said syringe, said piston hygienically sealing said syringe fluid contents during non-use of said IV pump and during the use thereof in response to said power stroke of said IV pump plunger urging said syringe fluid contents in exiting flow from said syringe, after which said syringe is disposed of preparatory to use of a replacement syringe, whereby the same IV pump is used with plural syringes.

2. An IV pump as claimed in claim 1 in which said sleeve is of clear plastic construction material through which the volumetric changes in the fluid contents of said syringe is readily observable.

3. An IV pump as claimed in claim 2, in which said IV pump plunger and each said syringe piston of said plural syringes are readily attachable and detachable to each other, to thereby facilitate the use of said IV pump successively with said syringes, one at a time.

4. An IV pump as claimed in claim 3 wherein said IV pump plunger and said syringe piston have cooperating interconnecting means characterized by a taper in each oriented in the direction of said IV pump power stroke, whereby the urgency of said power stroke results in a force fit of the one said taper with the other to contribute to the attachment of said IV pump plunger with said syringe piston.

* * * * *